US007584751B1

(12) United States Patent
Brooks, Jr. et al.

(10) Patent No.: US 7,584,751 B1

(45) Date of Patent: Sep. 8, 2009

(54) ADAPTER FOR PROTECTIVE MASK TESTING APPARATUS

(75) Inventors: Lowry J. Brooks, Jr., Fallston, MD (US); Chika N. Nzelibe, Hyattsville, MD (US); Joshua D. Israel, Baltimore, MD (US); Matthew D. Reber, Elkton, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 804 days.

(21) Appl. No.: 11/203,580

(22) Filed: Aug. 11, 2005

(51) Int. Cl.
*A61M 11/00* (2006.01)

(52) U.S. Cl. ............................ 128/201.19; 128/201.25; 73/49.8

(58) Field of Classification Search ............ 128/201.19, 128/201.22–201.28, 202.13, 202.18, 206.21, 128/202.22; 73/40, 40.5 R, 49.8, 866.5, 73/167
See application file for complete search history.

(56) References Cited

U.S. PATENT DOCUMENTS

| | | | | |
|---|---|---|---|---|
| 4,914,957 | A * | 4/1990 | Dougherty | 73/40 |
| 5,299,448 | A * | 4/1994 | Maryyanek et al. | 73/40 |
| 6,382,206 | B1 * | 5/2002 | Palazzotto et al. | 128/201.19 |
| 6,435,009 | B1 * | 8/2002 | Tilley | 73/40 |

* cited by examiner

*Primary Examiner*—Steven O Douglas
(74) *Attorney, Agent, or Firm*—Ulysses John Biffoni

(57) ABSTRACT

An adapter for testing an outlet valve of a protective mask with a testing apparatus includes portions which oppose the valve and are configured to connect the valve to the tester in sufficient isolation for testing purposes. In one implementation, the valve has first and second notches configured to engage corresponding non-uniform geometries in an interference fit. In still further implementations, the adapter comprises an overmold with a resiliently compressible surface conformed to mate with the outlet valve and an insert at least partly encapsulated by the overmold and providing support to the resilient compression of the surface of the overmold. In use, the portions of the adapter engaging corresponding locations on the valve to be tested form an interference fit.

12 Claims, 5 Drawing Sheets

ADAPTER FOR PROTECTIVE MASK TESTING APPARATUS

GOVERNMENTAL INTEREST

The invention described herein may be manufactured, used and licensed by or for the U.S. Government.

TECHNICAL FIELD

This invention relates to apparatus for testing protective masks, such as so-called gas masks.

BACKGROUND

There are a variety of protective masks or, colloquially, “gas masks,” to prevent users from inhaling toxic substances of all sorts. Such masks include negative pressure chemical, biological, radiological, and nuclear protective masks, known as CBRN protective masks in military parlance. The M45 joint service protective mask, part of the M40 series of masks, is among those in use by various branches of the United States Armed Services.

It is, of course, desirable to assure that the M45 masks and other protective masks in use by the military function and fit properly in order to protect the users from exposure to various toxins. In particular, the function of the outlet valve of the protective mask is often critical. Upon inhalation, the outlet valve must close to a sufficient degree to channel inhalation through the mask’s canister without drawing in toxins from outside the mask. Conversely, upon exhalation, the outlet valve must open sufficiently to expel the breath, again without unacceptable leakage.

The outlet valve and other features of protective masks may be tested at the manufacturing facility. Factory tests of the outlet valves of protective masks often suffer from certain drawbacks and disadvantages. For example, operation of the outlet valve is generally tested by applying positive or negative pressure to the valve from inside of the mask. Such test results are often not acceptable to the armed services or other users. Such “inside” tests differ from testing the function of the valve from outside of the mask, and therefore such outside testing is generally preferred as an indication of serviceability and reliability.

The joint service mask leakage tester (JSMLT, in military parlance) is a portable testing device that has been developed for testing certain protective masks. However, the results obtained from the JSMLT are generally only as good as the connection between the JSMLT and the protective mask to be tested. In other words, unless the mask to be tested is properly secured or connected to the JSMLT, the test results related to function, serviceability, leakage, and proper fit of the mask may be inaccurate, producing either false positives or false negatives. In addition to the JSMLT, other portable testers are available for use and also require a secure connection between the mask being tested and the test device. Some of these devices include the TDA-99M Protective Mask Leakage Tester, which is the commercial equivalent of the JSMLT, and the TDA-99B which are both available commercially from Air Techniques International (ATI), of Owings Mills, Md.

The current connections between the JSMLT and masks to be tested suffer from various drawbacks and disadvantages, especially with regard to masks having outlet valves of irregular geometry, such as the M45. Current connections to the JSMLT sometimes may not create a sufficient seal with the outlet valve for accurate testing purposes. Establishing a suitable connection may be a cumbersome process at times, the ability to achieve the suitable connection may be inconsistent at other times, and the resulting connection may be unreliable at still other times.

There is thus a need to address the various drawbacks and disadvantages of the current apparatus for testing protective masks.

SUMMARY

An adapter is provided for testing an outlet valve of a gas mask with a mask leakage testing apparatus. In one implementation, part of the adapter is an overmold having a resiliently compressible surface which has been conformed so as to mate with the outlet valve. The adapter has an insert formed of a material which is more rigid than that of the overmold. The insert is secured to the overmold in such a way that a surface of the insert at least partly underlies the conformed surface of the overmold. In this way, the insert surface provides support to the resilient compression of the conformed surface of the overmold. Certain portions of the conformed surface engage corresponding locations of the housing of the valve in an interference fit. As a result, the valve portion is sufficiently isolated for testing purposes by the apparatus.

In certain implementations, the adapter is part of a joint service mask leakage tester. The adapter in such implementations includes portions which oppose an M45 mask outlet valve to be tested. The portions which oppose the valve to be tested include first and second notches configured to engage, respectively, a drink tube and microphone connection port associated with the housing of the valve. Other portions of the adapter include multiple walls which engage corresponding locations on the valve in an interference fit.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
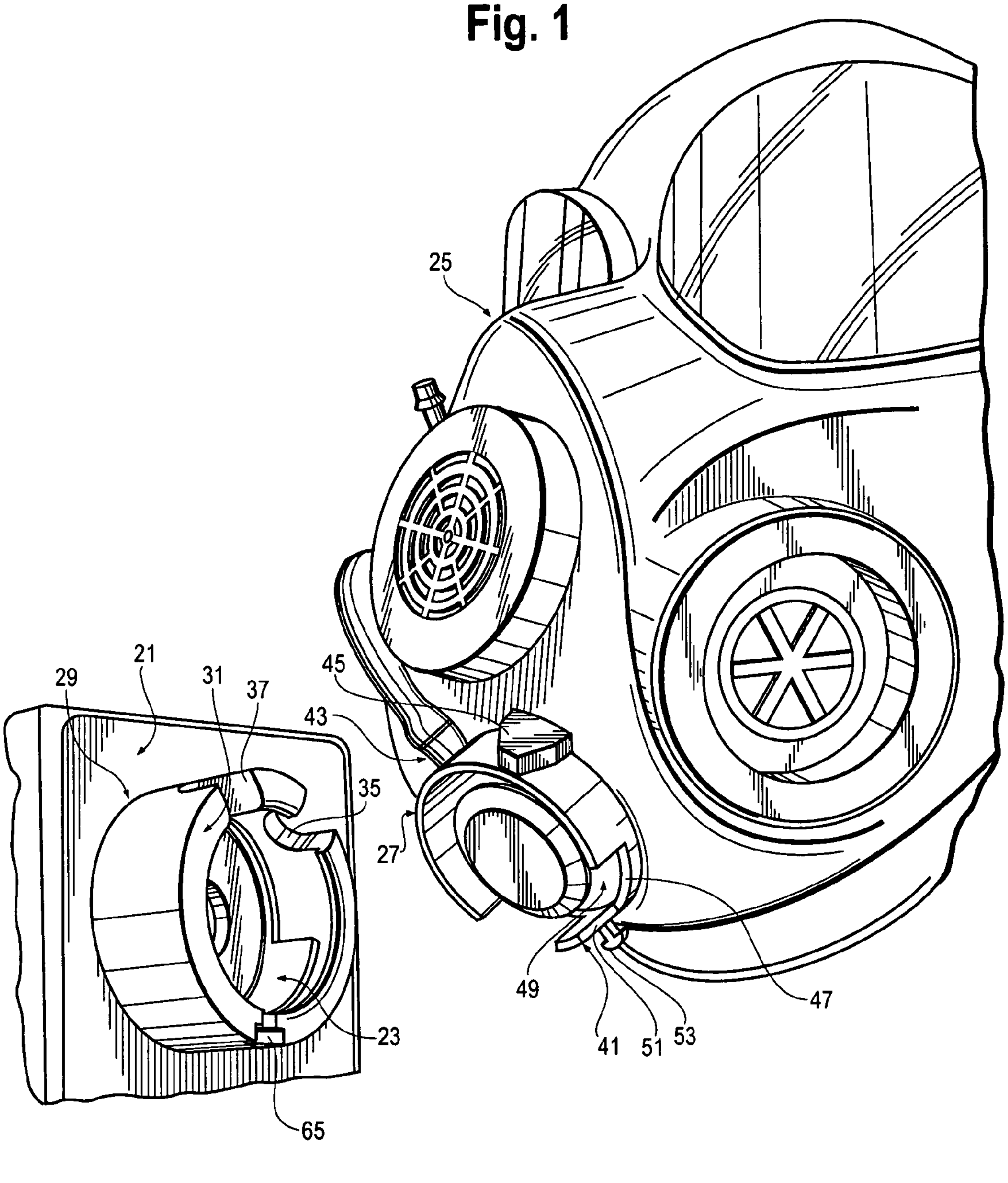
FIG. 1 is a perspective view of a testing apparatus, a mask to be tested, and an adapter for the apparatus.

Referring now to the drawings and, in particular, to FIG. 1, one suitable apparatus for testing protective masks 25 is as a joint service mask leakage tester (JSMLT) 21. The JSMLT tests a variety of functions and features of protective masks in order to determine mask serviceability, identify defective components, and perform quantitative factor tests. To test for outlet valve leakage and perform the other tests of interest, the JSMLT includes an aerosol generator assembly, control unit, power unit, head forms, an interface hose, a fit test module, and other components. The JSMLT is a military version of ATI's model number TDA-99M, which is described at ATI's website at www.atitest.com.

Figure 2:
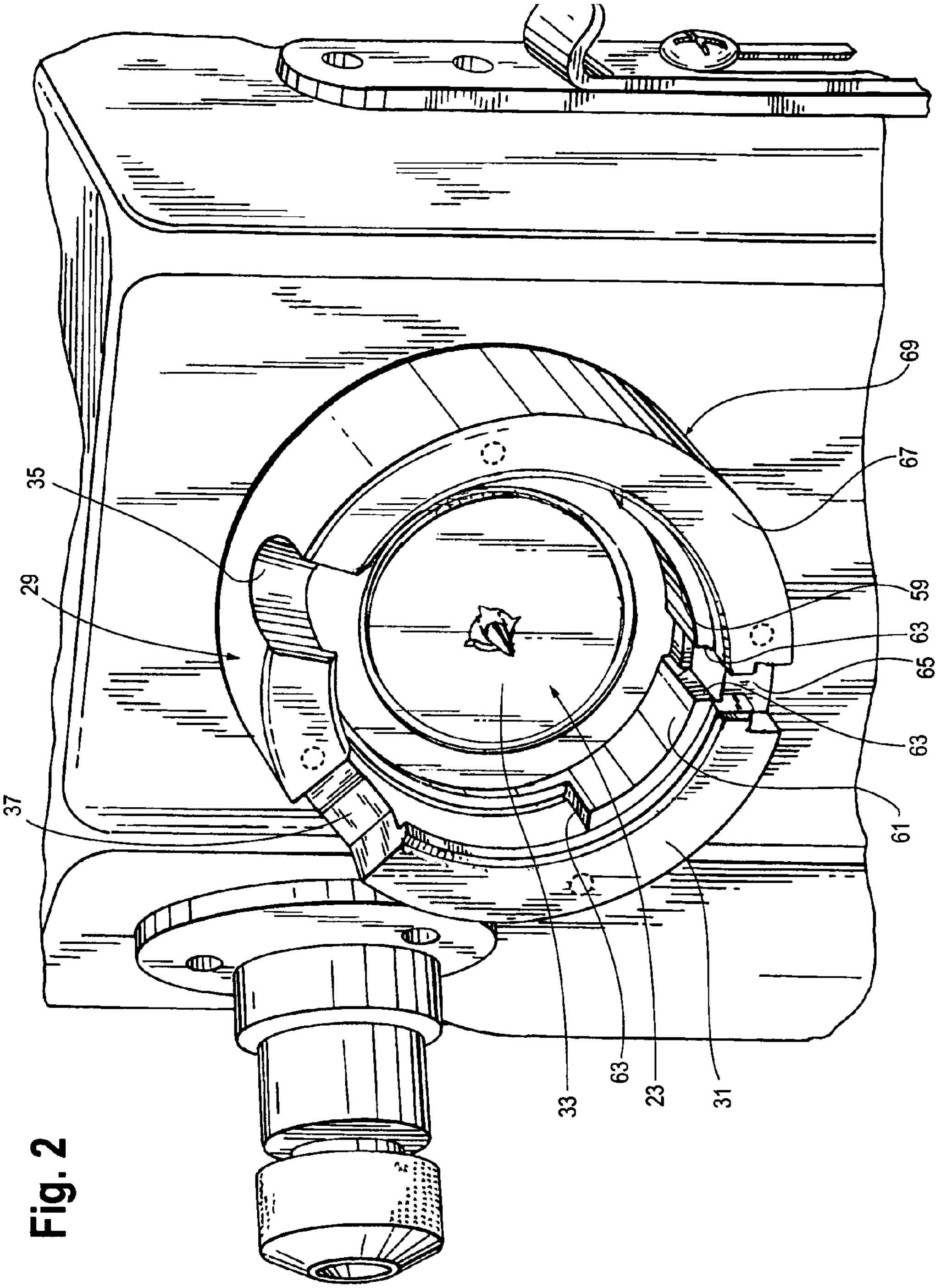
FIG. 2 is an enlarged, perspective view of the apparatus of FIG. 1.

As seen in FIGS. 1 and 2, testing apparatus includes a testing port 23 through which positive or negative air pressure is delivered for performing outlet valve leakage testing in a manner appreciated by those skilled in the art.

A protective mask 25, here shown as the M45 negative pressure mask, includes an outlet valve 27 to be tested with testing apparatus 21. To accomplish such testing, outlet valve 27 must be operatively connected to testing port 23. Such operative connection means that valve 27 is exposed to one or more tests through suitably isolated pneumatic communication with testing port 23.

Adapter 29 facilitates the operative connection between outlet valve 27 and testing apparatus 21. As seen in FIG. 2, adapter 29 includes a surface 31 which opposes valve 27. Surface 31 has been conformed or otherwise configured to connect valve 27 to testing apparatus 21 in sufficient isolation to test valve operation. Adapter 29 also includes a suitable connector 33 which secures adapter 29 in pneumatic communication with testing port 23.

Figure 5:
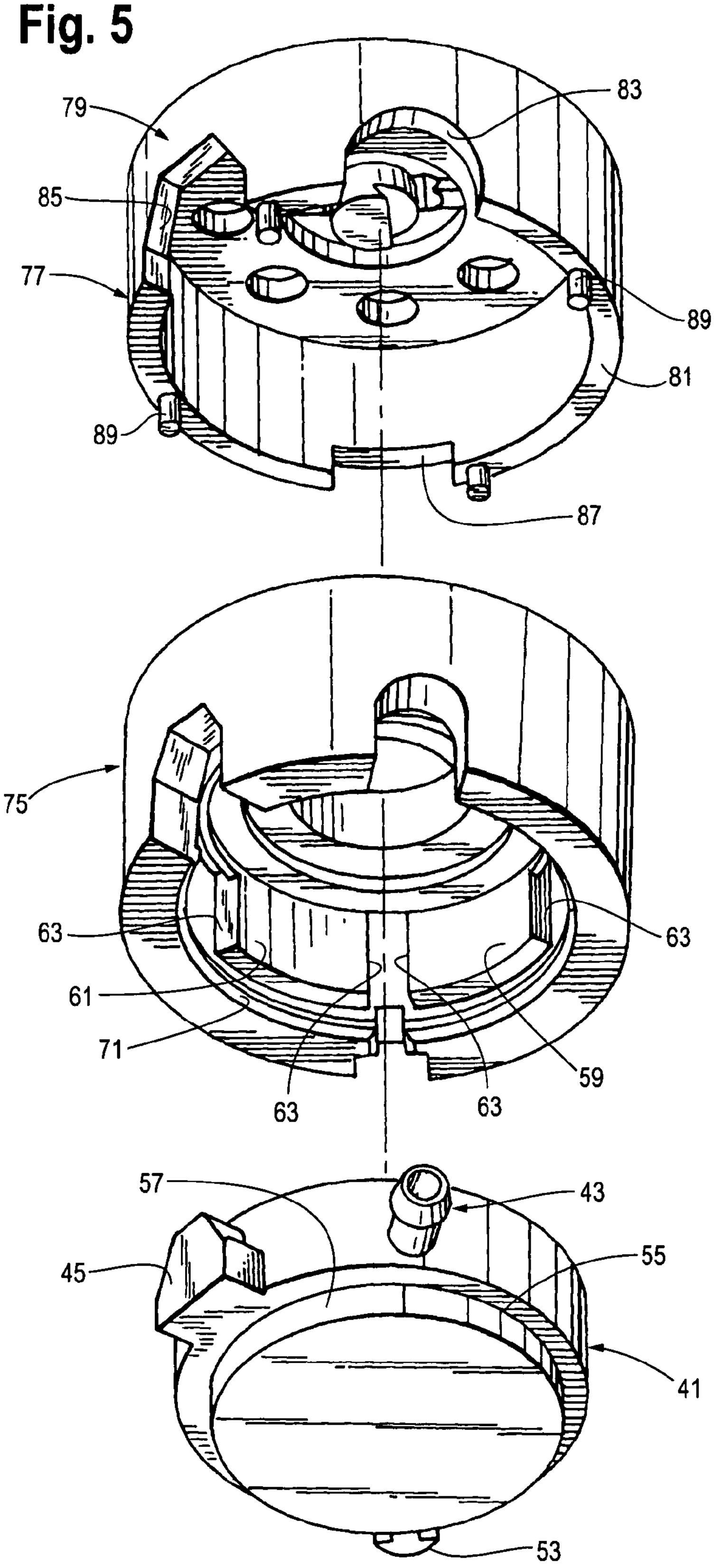
FIG. 5 is an exploded perspective view of the adapter and valve housing of the preceding figures.

As seen by reference to FIGS. 1 and 5, outlet valve 27 includes a valve housing 41. Valve housing 41 has various non-uniform geometries or portions which pose challenges to suitably connecting it to testing equipment. In this example and implementation, the non-uniform portions of housing 41 include a drinking tube (and associated fitting) 43 and a microphone connection port 45, both of which extend radially outwardly from a cylindrical sidewall 47 of housing 41. The uniformity of cylindrical sidewall 47 itself is interrupted by two gaps or breaks 49 which extend over an arc of about 30° each. Between the two breaks 49 is an isolated section 51 of sidewall 47, and a tab 53 (for securing a mask cover (not shown)). Tab 53 extends radially outwardly from section 51 and cylindrical sidewall 47, forming another non-uniform portion of housing 41 of valve 27. At the base of cylindrical sidewall 47 is a cylindrical wall 57 (FIG. 5) having a smaller diameter of curvature than that of cylindrical sidewall 47, thereby forming a detent 55 between walls 57, 47.

Figure 3:
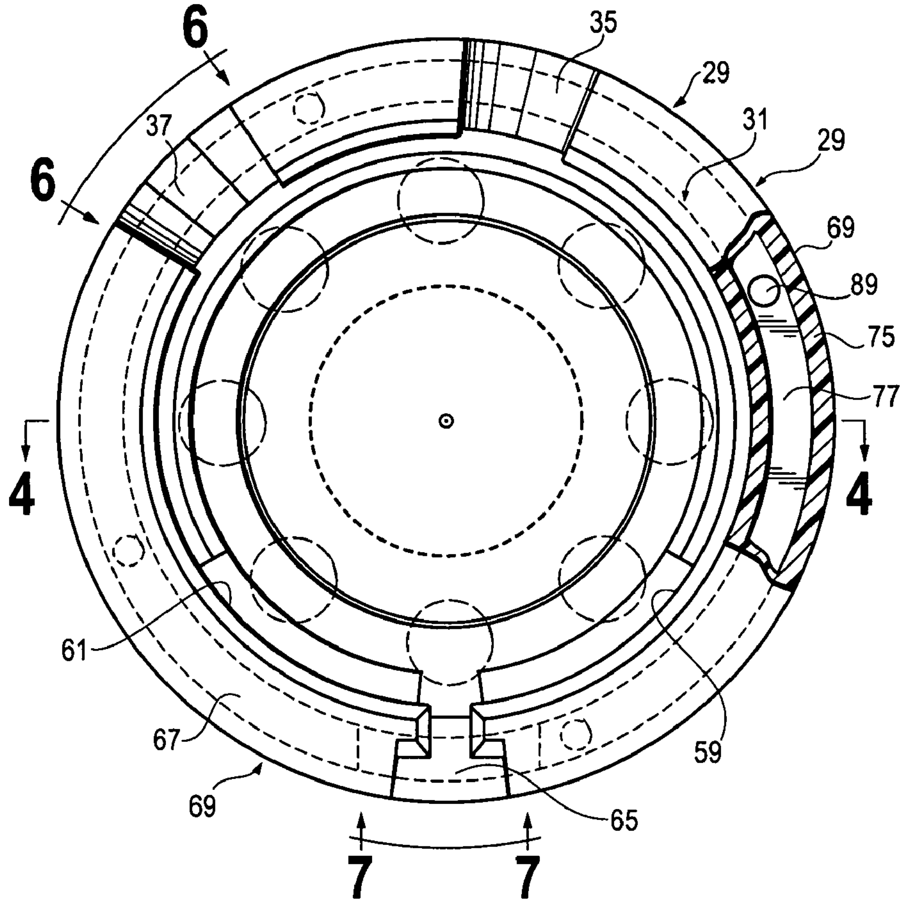
FIG. 3 is a top plan view of the adapter of FIGS. 1 and 2.
Figure 4:
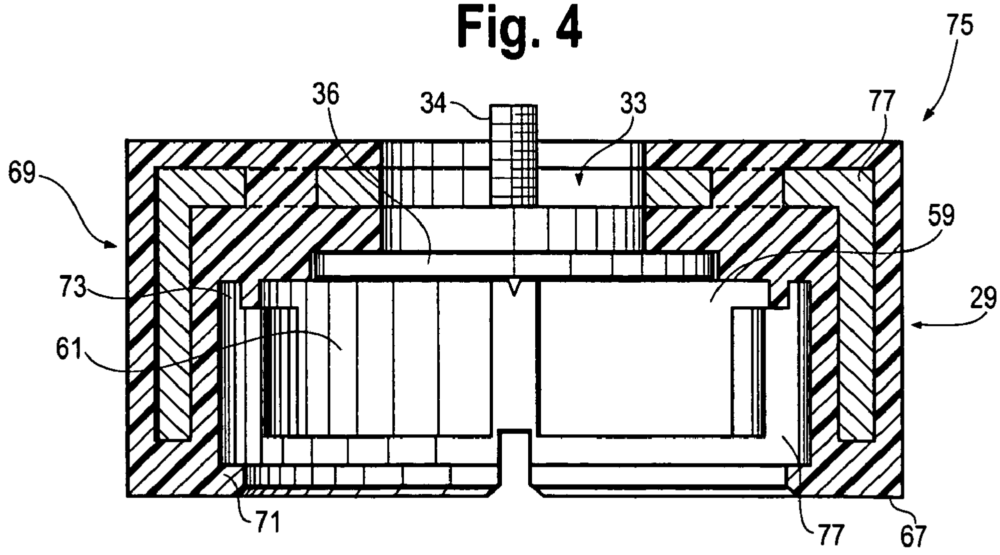
FIG. 4 is side elevational view along line 4-4 of the adapter shown in FIG. 3.

Referring now again to adapter 29 and FIGS. 2-4, in this implementation, surface 31 has been conformed to include various features or portions which engage corresponding locations on valve 27 to form an interference fit sufficient to connect valve 27 to testing apparatus 21. Surface 31 includes notches 35, 37 configured to engage drink tube 43 and microphone connection port 45, respectively, in an interference fit. Surface 31 also includes multiple walls for engaging valve 27. For example, two circumferential arcs 59, 61 are formed into surface 31 to mate with breaks 49 in housing 41 of the outlet valve 27. The circumferential arcs 59, 61 terminate in wall ends 63 which engage opposing portions of cylindrical sidewall 47 of housing 41 to form interference fits. A third notch 65 is sized to receive tab 53 therein in an interference fit.

Notches 35, 37, and 65 are defined in surface 67 of adapter 29. When adapter 29 is installed on testing apparatus 21, surface 67 faces outwardly from testing apparatus 21 and opposes mask 25 to be tested. Surface 67 thus is an upper or outer surface of adapter 29 as shown in the drawings of this implementation. Upper surface 67 is part of a generally cylindrical wall 69 which extends circumferentially at the perimeter of adapter 29. Notches 35, 37, 65 are positioned at angles around circumferential wall 69 so as to correspond to angular locations of drinking tube 43, microphone connection port 45, and tab 53, respectively, in outlet valve 27.

Similarly, circumferential arcs 59, 61 are disposed inwardly and near circumferential wall 69 of adapter 29, and at angular locations to mate with breaks or gaps 49 in sidewall 47 of valve housing 41.

Adapter 29 has a circumferential lip 71 extending inwardly at or near upper surface 67, and a circumferential crevice 73 at or near the base of cylindrical wall 69. Lip 71 is sized to resiliently compress as cylindrical sidewall 47 of outlet housing 41 is inserted into adapter 29. As best visualized by reference to FIG. 5, when housing 41 has been sufficiently advanced, lip 71 decompresses to engage detent 55 at the base of housing 41. Engagement of lip 71 into detent 55 provides the operator of testing apparatus 21 with a "snap in" feel that outlet valve 27 has been fully received onto adapter 29, as well as providing a sealing function. Crevice 73 receives therein an upper portion of cylindrical sidewall 47 in an interference fit.

Referring now more particularly to FIGS. 3-5, in this implementation, the various notches, walls, and other geometries of adapter 29 are defined by conforming an outer surface (corresponding to surface 31) of an overmold 75. Overmold 75 is formed of a resiliently compressible, polymeric material, preferably rubber, SANTOPRENE, or a soft elastomer, although other materials are likewise suitable. The resilient compressibility of the material for overmold 75 can vary in durometer from 20 to 80, such as between 20 and 50. A durometer of about 30 has been found well suited for this implementation. Overmold 75 surrounds or encapsulates an insert 77. Insert 77 is formed of a more rigid material than that used for overmold 75, such as aluminum, although other materials, such as nylon, or a more rigid polymeric material, are also suitable. By virtue of the more rigid material used for insert 77, it supports overmold 75 and aids the various features of conformed surface 31 in establishing the interference fit sufficient to isolate valve 27 for testing purposes. Thus, insert 77 has its own circumferential insert wall 79 with upper surface 81 underlying upper surface 67 formed in wall 67 of overmold 75. Similarly, insert 77 has cut-outs 83, 85, and 87 (FIG. 5) extending into insert wall 79 at angular locations corresponding to notches 35, 37, and 65, respectively, defined in overmold 75. Cut-outs 83, 85, and 87 are sized and dimensioned to underlie notches 35, 37, 65 when insert 77 has been encapsulated by overmold 75.

A plurality of pins 89 extend upwardly or outwardly (as shown in the drawings) from surface 81 of insert wall 79. Pins 89, when surrounded or encapsulated by overmold 75, aid in maintaining the angular registration between overmold 75 and insert 77.

To encapsulate insert 77, it is placed into a cavity of the mold corresponding to the overmold. The polymeric material for the overmold is then introduced into the cavity, which is then filled so as to encapsulate the insert and create the overmold.

It will be appreciated that the interference fit around each of the non-uniform portions of valve 27 needs to be sufficient to seal valve 27 to testing apparatus 21 for testing purposes. In other words, the interference fits created by the features of conformed surface 31 must not "leak" during testing. The existence of multiple, non-uniform geometries in valve 27, as well as the spacing of such non-uniformities at different angular locations around the circumference of housing 41, complicate the creation of a suitable interference fit for a variety of reasons. To address these complexities, the durometer of surface 31 must be sufficiently hard to remain sealed when exposed to positive and negative pressures of testing, yet sufficiently soft to conform to the non-uniform or irregular geometries of valve 27.

Once an appropriate durometer or range of durometer is selected, the presence of angles and edges in the geometry of valve 27 still may make the valve prone to leakage or other unsealing, as such angles and edges may create sufficient stress concentrations to separate opposing portions of adapter 29 from valve 27—even when such opposing portions are made of resiliently compressible material. Furthermore, the creation of suitable interference fits with resiliently compressible material is generally accompanied by a certain amount of "push back" force caused by its compression. While such "push back" force is desirable for the purposes of forming the interference fit, if such forces are greater at one angular location around the circumference of adapter 29 than at other such locations, there is a possibility that adapter 29 will "rock" in response to such unbalanced force, causing a gap in certain interference fits and unacceptable leakage.

In view of the foregoing, notches 35, 37, and 65, the other features of adapter 29, and the corresponding underlying portions of insert 77 have dimensions selected for this implementation to achieve the desired interference fit. For example, notch 35 has a width of about 0.4 inches at upper surface 67, a maximum depth of about 0.5 inches, with a radius of about 0.2 inches at the bottommost extension of notch 35. The corresponding cut-out 83 has a width of about 0.6 inches at upper surface 81, a maximum depth of about 0.4 inches, and a radius of curvature of about 0.3 inches defining the bottom area of cut-out 83. Upper surface 67 of overmold 75 is spaced from upper surface 81 of insert 77 by about 0.175 inches.

Figure 6:
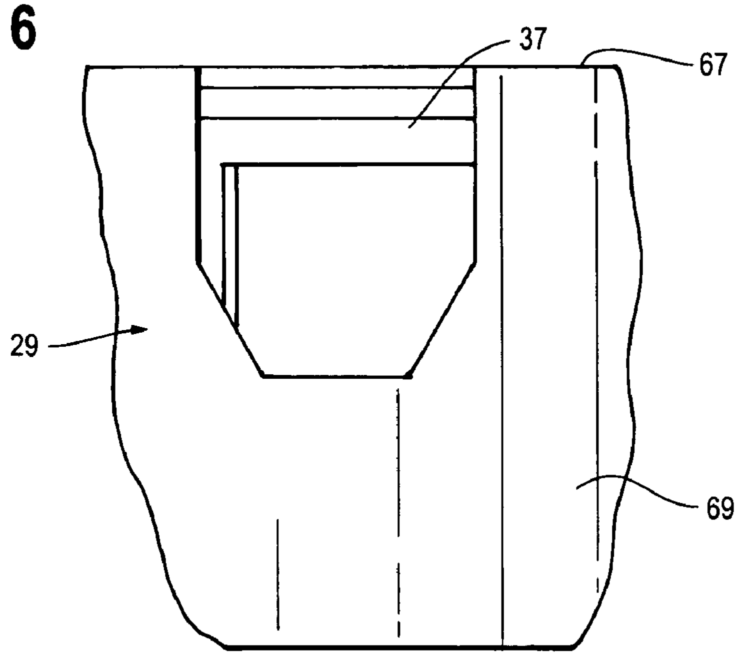
FIG. 6 is a partial, side elevational view of a portion of the adapter taken along line 6-6 of FIG. 3.

Notch 37 comprises a five-sided channel, as best seen in FIG. 6, with a width of about 0.47 inches at upper surface 67, a maximum depth of about 0.54 inches, a pair of vertically oriented sidewalls extending about 0.34 inches from upper surface 67, and a pair of sidewalls angled inwardly from such vertical sidewalls by about 30°. Cut-out 85 in insert 77 corresponds to notch 37 and likewise has a five-sided trough, with a width of about 0.67 inches, a maximum depth of about 0.42 inches, a pair of vertically descending sidewalls of about 0.15 inches, and a pair of sidewalls extending inwardly to the bottom of the trough from the vertical side walls at an angle of about 30°.

Figure 7:
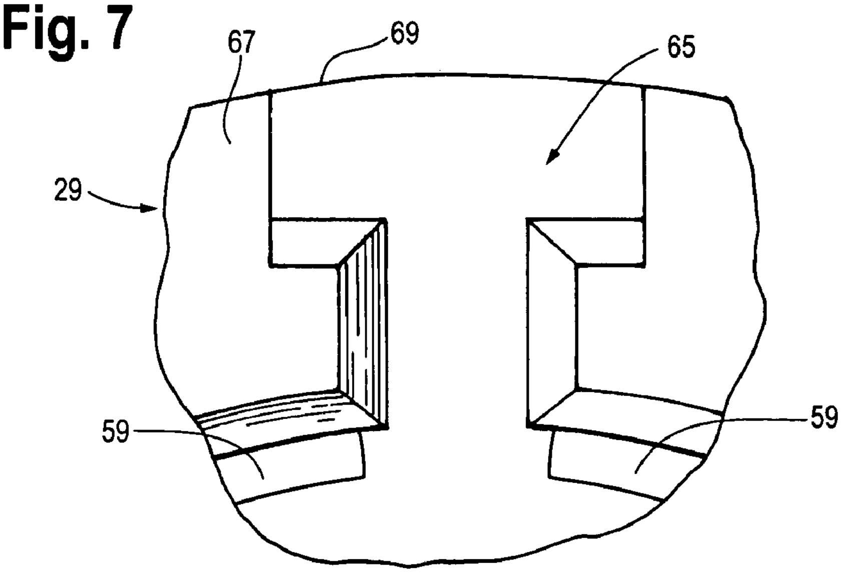
FIG. 7 is a partial, top plan view of the adapter taken along line 7-7 of FIG. 3.

Referring now to FIG. 7, notch 65 comprises a T-shaped trough with a width of about 0.122 inches at the outer edge of cylindrical wall 69, depth of about 0.198 inches, and two pairs of champhered surfaces restricting the width to about 0.12 inches near the inner edge of cylindrical wall 69. Cut-out 87 in insert 77 corresponds to notch 65, and comprises a channel having a similar or identical width and depth.

Of course, while these particular dimensions have been found suitable of this application, the invention is not limited to such dimensions nor this application, and other sizes, configurations, and applications are clearly contemplated. Connector 33 may assume any number of forms suitable to secure adapter 29 to testing apparatus 21. In this implementation, connector 33 includes a disc 36 of rigid material seated or otherwise received within the space defined by cylindrical wall 69. A threaded shank 34 extends longitudinally outwardly from the disc sufficiently to be received in a complementarily threaded bore in testing apparatus 21.

Operation of testing apparatus 21 and associated adapter 29 is readily apparent from the foregoing description. Adapter 29 is suitably secured to testing apparatus 21 to be in operative association with test port 23. Outlet valve 27 is positioned in front of adapter 29 and at an angular orientation to match up the radially extending, irregular geometries of valve 27 with corresponding notches 35, 37, and 65 in adapter 29. Mask 25 is manipulated to insert outlet valve 27 into adapter 29. Valve 27 is advanced relative to cylindrical wall 69 and into adapter 29 until lip 71 of adapter 29 engages detent 55 of housing 41, such engagement being generally physically perceptible to the user of testing apparatus 21 and overall seal. An interference fit is created by the engagement of valve 27 against corresponding, resiliently compressible portions of adapter 29. Outlet valve 27 is then subjected to one or more tests which act on the valve portion of valve 27.

A number of embodiments of the invention have been described. Nevertheless, it will be understood that various modifications may be made without departing from the spirit and scope of the invention. For example, while the adapter 29 in this implementation includes an overmold and an encapsulated insert, use of two pieces is not required. Alternately, the overmold and insert can be replaced with a single component, either machined, molded, or otherwise formed to include portions for opposing and engaging corresponding locations on the valve to be tested.

As a related alternative, there is no need for various portions of adapter 29 to be defined integrally in or on a surface, or, for that matter, to be defined by conforming a surface through molding or machining. In other words, portions for mating or engaging corresponding locations on valve 27 can be provided to adapter 29 by fastening one or more pieces to adapter 29 at the appropriate locations. Thus, adapter 29 can be provided with portions for engaging valve 27 by affixing one or more discrete geometries relative to each other at suitable locations.

Similarly, adapter 29 can be equipped with adjustable or variable portions which move relative to each other to provide the necessary engagement with valve 27. It is likewise understood that the sizes and shapes of the portions of adapter 29 which engage corresponding locations on valve 27 can be varied to suit any number of outlet valves for any number of protective masks. Furthermore, although the portions of adapter 29 in the illustrated implementations include notches, surfaces, and walls, still other geometries may be appropriate and suitable to provide the necessary engagement and interference fit with corresponding locations of certain outlet valves. So, for example, bores, steps, teeth, tongues, or other extensions, depressions, or geometries can be arranged on the adapter in a way to oppose corresponding locations on the outlet valve and achieve the desired seal with such valve.

It is understood that still further variations and modifications may be made without departing from the spirit and scope of the invention, and that the implementations and alternatives presented herein are not intended to limit the inventions, the scope of which is set out in the following claims.

What is claimed is:

1. In a mask leakage tester, the improvement comprising an adapter for testing a mask outlet valve, the valve having a drink tube and a microphone connection port associated therewith, the adapter comprising portions opposing the valve and configured to connect the valve to the tester in sufficient isolation to test operation of the valve, wherein the portions include first and second notches configured to engage the drink tube and the microphone connection port, respectively, in an interference fit and wherein the adapter further comprises an overmold, wherein the overmold comprises a resiliently compressible polymeric material and herein the overmold has a surface defined thereon, wherein the portions of the adapter opposing the valve are defined by the surface of the overmold, wherein the adapter further comprises an insert secured to the overmold and having an insert surface at least partly underlying the surface of the adapter defined by the overmold; and wherein the insert is formed of a more rigid material than the overmold, the insert surface providing support for resilient compression of the surface defined on the overmold to facilitate engagement of the adapter and the valve to be tested.

2. The tester of claim 1, wherein the portions of the adapter further include multiple walls for engaging corresponding locations of the valve in an interference fit.

3. The tester of claim 2, wherein the walls include two circumferential arcs, each are terminating in opposite wall ends engaging the valve in an interference fit.

4. The tester of claim 1, wherein the mask outlet valve to be tested further includes a valve housing having non-uniform portions extending radially outwardly, and wherein the portions of the adapter are further configured to receive at least part of the non-uniform portions of the valve housing therein in an interference fit.

5. The tester of claim 1, wherein the portions are integrally formed on a surface of the adapter.

6. The tester of claim 5, wherein the surface is molded to define the portions.

7. An adapter for testing an outlet valve of a protective mask with a testing apparatus, the outlet valve having a valve portion and a housing, the adapter comprising:

an overmold having a resiliently compressible surface conformed to mate with the outlet valve; and an insert formed of a more rigid material than the overmold, operatively associated with the overmold, and having an insert surface at least partly underlying the conformed surface of the overmold to provide support for resilient compression of the surface of the overmold;

wherein the conformed surface includes portions engaging corresponding locations of the valve housing in an interference fit to isolate the valve portion sufficiently for testing by the apparatus.

8. The adapter of claim 7, wherein the portions of the conformed surface include multiple notches.

9. The adapter of claim 8, wherein the portions of the conformed surface include a cylindrical wall having a base and an upper surface, and wherein the notches are formed in the upper surface.

10. The adapter of claim 9, wherein the portions of the conformed surface further include a lip extending inwardly at or near the upper surface of the cylindrical wall, and a circumferential crevice at or near the base of the cylindrical wall.

11. The adapter of claim 9, wherein the portions of the conformed surface include multiple walls extending through arcs to terminate in wall ends, the wall ends engaging the valve in an interference fit.

12. The adapter of claim 7, wherein the outlet valve to be tested comprises an outlet valve having an associated drink tube and microphone connection port, and wherein the portions of the conformed surface include notches engaging the drink tube and the microphone connection port.

* * * * *